United States Patent
Lytinas

(10) Patent No.: US 8,423,148 B1
(45) Date of Patent: Apr. 16, 2013

(54) METHOD FOR TREATING CARTILAGE DEFECTS

(76) Inventor: Michael Lytinas, Boston, MA (US)

( * ) Notice: Subject to any disclaimer, the term of this patent is extended or adjusted under 35 U.S.C. 154(b) by 1366 days.

(21) Appl. No.: 12/049,666

(22) Filed: Mar. 17, 2008

Related U.S. Application Data

(60) Provisional application No. 60/918,676, filed on Mar. 19, 2007.

(51) Int. Cl.
*A61N 1/44* (2006.01)
(52) U.S. Cl.
USPC .............................. 607/50; 607/51
(58) Field of Classification Search ............... 607/50, 607/51
See application file for complete search history.

(56) References Cited

U.S. PATENT DOCUMENTS

| | | | | |
|---|---|---|---|---|
| 4,702,732 A | * | 10/1987 | Powers et al. | 604/20 |
| 5,236,456 A | * | 8/1993 | O'Leary et al. | 623/23.63 |
| 5,433,735 A | * | 7/1995 | Zanakis et al. | 607/50 |
| 6,235,316 B1 | * | 5/2001 | Adkisson | 424/548 |
| 2002/0042633 A1 | * | 4/2002 | Markoll | 607/36 |
| 2004/0006373 A1 | * | 1/2004 | Brighton et al. | 607/1 |
| 2004/0267333 A1 | * | 12/2004 | Kronberg | 607/72 |

* cited by examiner

*Primary Examiner* — Christopher D Koharski
*Assistant Examiner* — Natasha Patel
(74) *Attorney, Agent, or Firm* — Barlow, Josephs & Holmes, Ltd.

(57) ABSTRACT

The present invention provides a method for treating at least one of the following: osteoarthritis, rheumatoid arthritis, cartilage injury, and a cartilage defect containing the following steps. First, a defective cartilage tissue is provided. Second, a solution containing ions for treating defective cartilage tissue is provided. Third, the solution containing ions is introduced about the defective cartilage tissue. Fourth, an electrical source generates electricity. Fifth, the solution containing ions and an area about the defective cartilage tissue is contacted with the electricity from the electrical source. Sixth, the electrical source is powered on to provide electricity, whereby the ions move from the solution and into the defective cartilage tissue.

19 Claims, 7 Drawing Sheets

METHOD FOR TREATING CARTILAGE DEFECTS

CROSS-REFERENCE TO RELATED APPLICATION

This application is related to and claims priority from earlier filed provisional patent application Ser. No. 60/918,676 filed Mar. 19, 2007.

BACKGROUND OF THE INVENTION

The present invention generally relates to treating cartilage defects. More specifically, the present invention relates to a method for treating cartilage defects, for example osteoarthritis, rheumatoid arthritis, and cartilage injuries, by moving ions into a collagen matrix of the defective cartilage using electricity.

Human joint surfaces are covered by articular cartilage, a low friction, durable material that distributes mechanical forces and protects the underlying bone. Injuries to articular cartilage are common, especially in the knee. Data from the Center for Disease Control (CDC) and clinical studies have suggested that approximately 100,000 articular cartilage injuries occur per year in the United States. Such injuries occur most commonly in young active people and result in pain, swelling, and loss of joint motion. Damaged articular cartilage does not heal. Typically, degeneration of the surrounding uninjured cartilage occurs over time resulting in chronic pain and disability. Cartilage injuries therefore frequently lead to significant loss of productive work years and have enormous impact on patients' recreation and lifestyle.

Generally, there are three main types of cartilage: hyaline cartilage, elastic cartilage, and fibrocartilage. Hyaline cartilage is the most abundant type of cartilage. Hyaline cartilage lines the bones in articular joints and also serves as a center of ossification. Elastic cartilage mainly provides support and elasticity, for example, in the pinna of the ear or in the larynx. It is similar to articular cartilage but contains elastin throughout the matrix. Fibrocartilage is found in the areas that require tough support or tensile strength, for example in the pubic area. It has more collagen than the other types of cartilage which gives it strength. Fibrocartilage replaces hyaline cartilage or articular cartilage in osteoarthritis.

Hyaline cartilage or articular cartilage is mainly the important architectural form of the tissue, which has multiple zones. Each zone, such as a superficial, middle and deep zone, has a role in the physiology of the cartilage. In the superficial zone, the collagen fibers run parallel to the surface. The superficial zone is most exposed to loading and has the highest tensile property.

Articular cartilage has four main components: collagen fibers, chondrocytes, water, and proteoglycans. Collagen fibers are responsible for the form and tensile properties of the tissue. Chondrocytes maintain the matrix. Water is about 80% by wet weight (FCD) in the tissue. Water content is governed by the FCD (Fixed Charged Density) of proteoglycans. A high concentration of proteoglycans, predominantly aggrecans, is responsible for the osmotic swelling that exerts on the collagen network. It is the retention of aggrecan in compressed form within the collagen network that causes the swelling pressure and makes cartilage ideal for resisting compressive loads, thereby supporting its function as a tough and resilient load-bearing surface.

The stiffness of cartilage is determined by the interaction of the three phases of cartilage: collagen fibers, proteoglycans, and the water. In other words, the load-bearing of cartilage is provided by the tensile properties of the collagen fibers and osmotic swelling pressure of aggrecan.

Referring to FIGS. 1A-1B, osteoarthritis is where cartilage degeneration is associated with loss of structural and functional integrity. For comparison, FIG. 1A shows a normal joint and an osteoarthritic joint (FIG. 1B) with a breakdown of cartilage. Osteoarthritis is not an inflammatory disease but it becomes inflamed after several pieces of cartilage are freed from the tissue inside the synovial fluid. Early swelling of cartilage leads through the dilution of proteoglycans, mainly aggrecans, out of the tissue to increased hydraulic permeability and decreased osmotic pressure. Increased hydraulic permeability means that water starts to flow into cartilage where it is not retained by the aggrecan since they are diluted in the synovial fluid. Afterwards, the collagen matrix starts to break down and deteriorate.

Currently, there are many treatments for the symptoms of osteoarthritis including: exercise, weight control, stress relief, drugs, surgery, and biologics. Biologics are a more recent treatment that includes autologous chondrocyte implantation, sterile artificial matrices, and hyaluronan.

However, non-steroidal anti-inflammatory drugs (NSAIDs) remain the primary treatment modality for osteoarthritis. It is unknown whether the efficacy of NSAIDs is dependent upon their analgesic or anti-inflammatory properties or the slowing of degenerative processes in the cartilage. There is also a concern that NSAIDs may be deleterious to patients. For example, NSAIDs have well known toxic effects in the stomach, gastrointestinal tract, liver and kidney. However, aspirin inhibits proteoglycan synthesis and normal cartilaginous repair processes in animals. One study in humans suggested that indomethacin might accelerate breakdown of hip cartilage. All adverse effects appear more commonly in the elderly—the very population most susceptible to osteoarthritis.

Therefore, there remains a need for an effective treatment of cartilage defects. There is a need for a method of replacing the proteoglycans missing in a collagen matrix due to cartilage defects. There is also a need for a method for treating cartilage defects that maintains the balance between the three phases of cartilage. Also, there is a further need for a method of treating cartilage defects without any adverse side effects and minimal invasive surgery. Finally, there is a need to provide a method for treating cartilage defects which controls pain, improves joint function, maintains normal body weight, and achieves a health lifestyle.

SUMMARY OF THE INVENTION

An embodiment of the present invention preserves the advantages of prior methods for treating cartilage defects. In addition, it provides new advantages not found in currently available methods for treating cartilage defects and overcomes many disadvantages of such currently available methods for treating cartilage defects.

The present invention provides a method for treating at least one of the following: osteoarthritis, rheumatoid arthritis, cartilage injury, and a cartilage defect containing the following steps. The method for treating cartilage defects can be used in a clinical setting which is outlined in the steps below. A defective cartilage tissue is provided. Typically, the defective cartilage tissue will have some collagen matrix intact and an absence of proteoglycans.

A solution containing ions for treating defective cartilage tissue is provided. The solution containing ions is selected from a group consisting of: proteoglycan solution, aggrecan isolation, chondrotin sulfate, and glucosamine. The proteoglycan solution is extracted from a non-defective cartilage tissue by guanidinization. The non-defective cartilage tissue is natural cartilage, synthesized, or a product of tissue engineering. The solution containing ions is introduced about the defective cartilage tissue, and more specifically into the collagen matrix of the defective cartilage tissue.

By using the principle of electrolysis, the ions then move from the solution and into the collagen matrix of the defective cartilage tissue. An electrical source provides electricity. The solution containing ions and an area about the defective cartilage tissue are contacted with the electricity from the electrical source. Next, the electrical source is powered on whereby the ions move from the solution and into the defective cartilage tissue. In one embodiment, the defective cartilage tissue is then dialyzed to remove the guanidine to allow aggrecan to reaggregate.

In one embodiment of the present invention, the method for treating cartilage defects is performed using an apparatus, such as a probe. In addition to the steps above, the apparatus is filled with the solution containing ions for treating cartilage defects. In one embodiment, the ions are negatively charged. The first end of the electrical source is connected to the apparatus containing the solution containing ions. In one embodiment, the first end of the electrical source is an anode. The defective cartilage tissue is contacted with the apparatus. A second end of the electrical source contacts an area about the defective cartilage tissue. In one embodiment, the second end of the electrical source is a cathode. When the electrical source is powered on, the negatively charged ions move towards the cathode and into the collagen matrix of the defective cartilage tissue.

The method for treating cartilage defects may also be performed in a laboratory setting as outlined in the steps below. A defective cartilage tissue is provided having a collagen matrix and an absence of proteoglycans. Proteoglycans in the defective cartilage tissue are destroyed leaving behind a collagen matrix. In one embodiment, the proteoglycans in the defective cartilage tissue are destroyed by trypsinization. A non-defective cartilage tissue is provided either natural, synthesized, or a product of tissue engineering. Next, the proteoglycans are extracted in a solution from the non-defective cartilage tissue using guanidinization. The extracted proteoglycan solution is introduced into the collagen matrix of the defective cartilage tissue.

By using the principle of electrolysis, the proteoglycans then move from the proteoglycan solution and into the collagen matrix of the defective cartilage tissue. An electrical source provides electricity. The extracted proteoglycan solution and an area about the defective cartilage tissue conducts the electricity from the electrical source. The electrical source is powered on whereby the proteoglycans move from the extracted proteoglycan solution and into the collagen matrix of the defective cartilage tissue. Afterwards, the defective cartilage tissue is dialyzed to remove the guanidine to allow aggrecan to reaggregate.

It is therefore an object of the method for treating cartilage defects to move ions into a collagen matrix of defective cartilage using electricity.

It is a further object of the method for treating cartilage defects that maintains a balance between the three phases of cartilage.

There is another object of the method for treating cartilage defects with minimal adverse side effects and surgery.

Another object of the method for treating cartilage defects to provide a method which controls pain, improves joint function, maintains normal body weight, and achieves a healthy lifestyle.

BRIEF DESCRIPTION OF THE DRAWINGS

The novel features which are characteristic of the method for treating cartilage defects are set forth in the appended claims. However, the method for treating cartilage defects, together with further embodiments and attendant advantages, will be best understood by reference to the following detailed description taken in connection with the accompanying drawings in which:

DETAILED DESCRIPTION OF THE PREFERRED EMBODIMENTS

Generally, the present invention solves the problems in methods for treating cartilage defects by providing a new and unique method for treating cartilage defects 10. More specifically, the present invention relates to a method for treating cartilage defects 10, by moving proteoglycans, or other ions, into the collagen matrix of the defective cartilage using electricity.

Figures 1A, 1B:
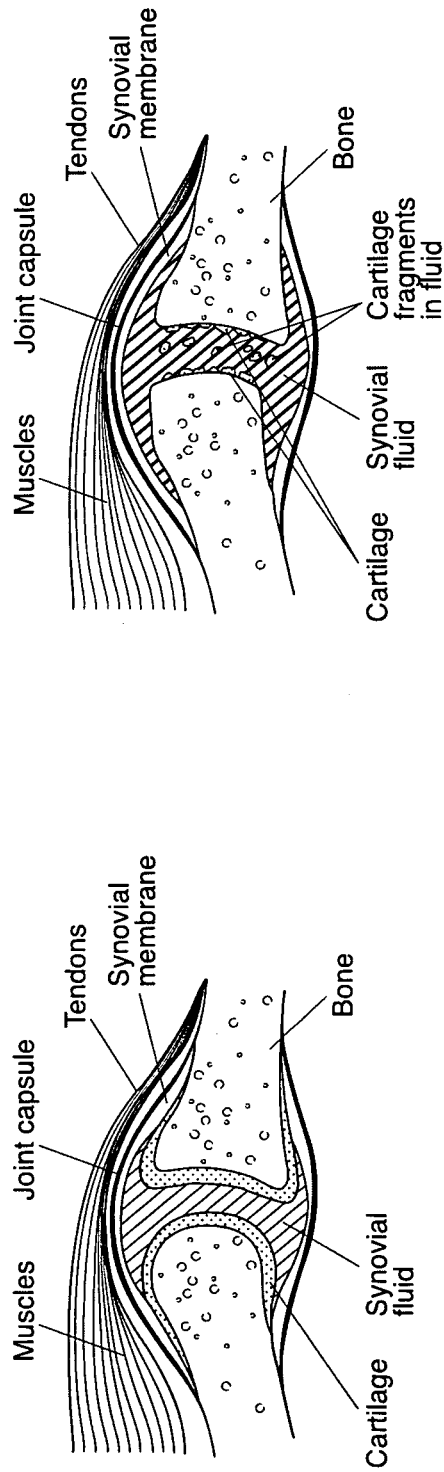
FIG. 1A is a prior art cross-sectional view of a healthy joint.
FIG. 1B is a prior art cross-sectional view of a joint with osteoarthritis.
Figure 2:
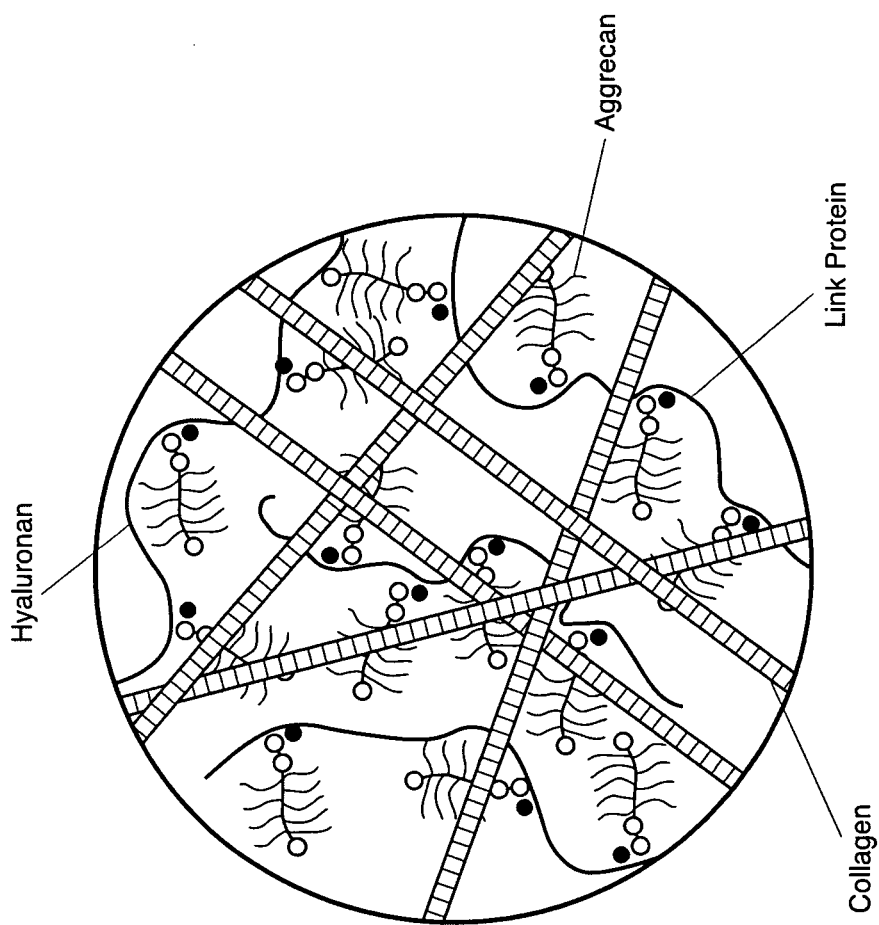
FIG. 2 is a plan view of cartilage tissue with proteoglycans.

By way of background, FIG. 2 illustrates healthy cartilage tissue having collagen matrix, proteoglycans, and water. The proteoglycans, mainly aggrecan, provide load-bearing for cartilage through osmotic swelling pressure. The collagen matrix provides tensile properties of the cartilage tissue. It is the interaction of all three phases of the cartilage—collagen matrix, proteoglycans, and water—which provides the stiffness of a cartilage.

Figure 3:
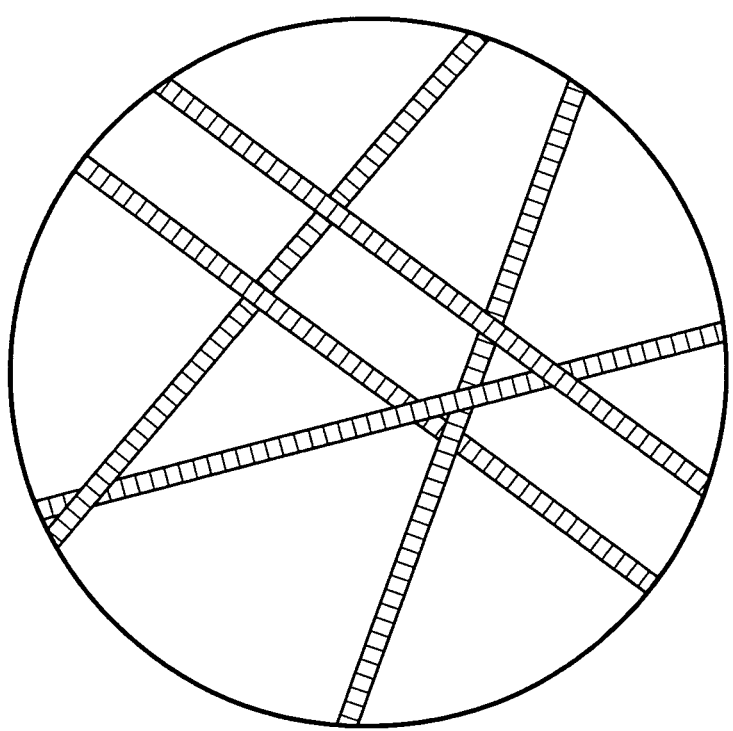
FIG. 3 is a plan view of cartilage tissue without proteoglycans.

FIG. 3 illustrates defective cartilage tissue missing proteoglycans. In defective cartilage tissue, the aggrecan leaves the collagen matrix to increase hydraulic permeability. This leads to decreased osmotic pressure and collagen matrix deterioration. The present method for treating cartilage defects 10 moves the proteoglycans back into the collagen matrix to provide healthier cartilage tissue.

Figure 4:
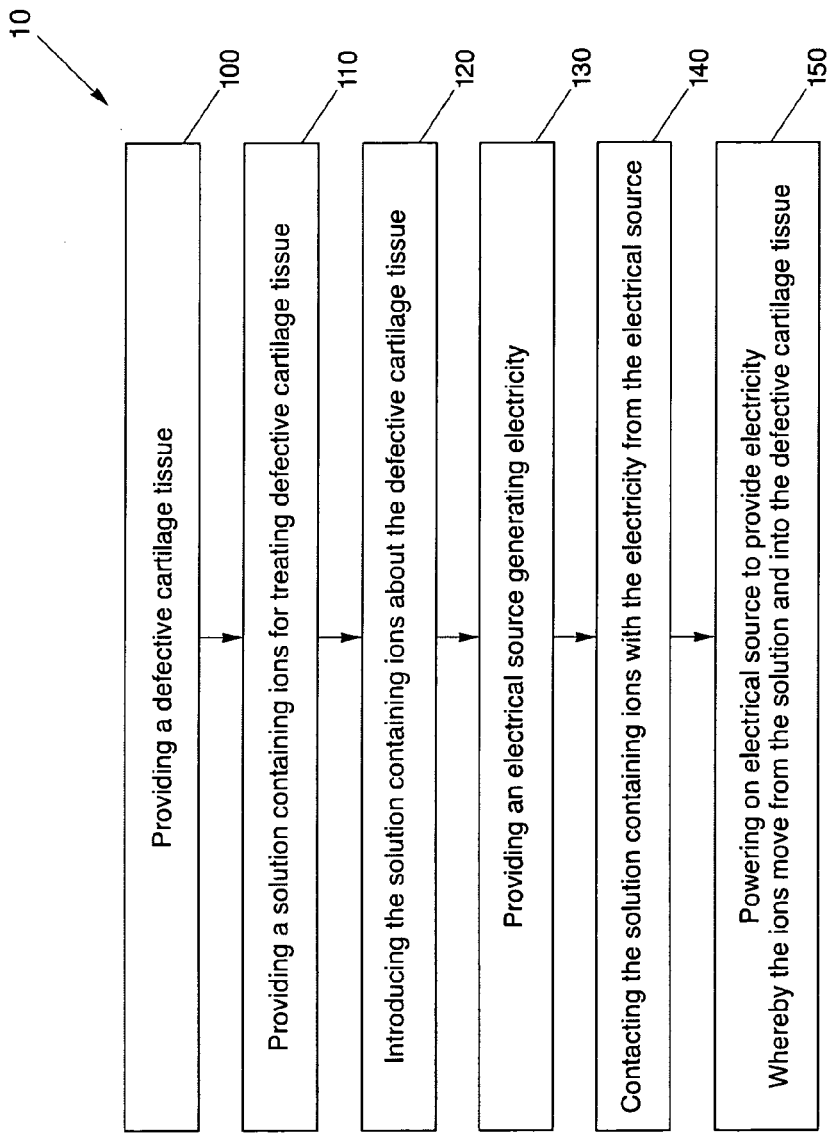
FIG. 4 is a block diagram of the present method for treating cartilage defects.

Referring to FIG. 4, the present invention provides a method for treating cartilage defects 10 by moving ions, such as proteoglycan, into a collagen matrix of defective cartilage using electricity. It should be noted that the present invention provides a method for treating at least one of the following: osteoarthritis, rheumatoid arthritis, cartilage injury, and other cartilage defects.

The method for treating cartilage defects can be used in a clinical setting and a laboratory setting. In a clinical setting, a defective cartilage tissue is first provided having a collagen matrix 100. Preferably, the collagen matrix is substantially intact to allow for ions to return. Typically, the defective cartilage tissue will have some collagen matrix intact and an absence of proteoglycans. Typically, the defective cartilage tissue is inside a human being or animal which has a cartilage defect and, most likely, devoid of proteoglycans. However, the defective cartilage tissue may be isolated, synthesized, and external to any living being.

In some cases, the defective cartilage tissue may be required to undergo trypsinization to destroy the proteoglycans and leave behind the intact collagen matrix. Tyrpsin is a protease that hydrolyses proteins and cleaves them into smaller peptides. The purpose of the trypsinization is to create space in the collagen matrix by destroying all aggrecan in the defective cartilage tissue while still preserving the collagen matrix.

The solution containing ions is selected from a group consisting of: proteoglycan solution, aggrecan isolation, chondrotin sulfate, glucosamine, or combinations thereof 110. In a preferred embodiment, the ions contained in the extracted proteoglycan solution or aggrecan isolation are utilized. The ions of the extracted proteoglycan solution are highly negatively charged ions but ions may be charged negatively or positively.

A solution containing ions is then introduced about the defective cartilage tissue, and more specifically into the collagen matrix of the defective cartilage tissue 120. Without being bound to any particular theory, it is believed that chondrotin sulfate and glucosamine may also be effective in treating cartilage defects. According to a study by the NIH entitled "Glucosamine/Chondroitin Arthritis Intervention Trial (GAIT)" http://nccam.nih.gov/research/results/gait/qa.htm, there has been evidence to suggest that chondrotin sulfate and glucosamine are more effective in treating cartilage defects when combined.

The proteoglycan solution is extracted from a non-defective cartilage tissue by guanidinization. The non-defective cartilage tissue is natural cartilage, synthesized, or a product of tissue engineering. Guanidinzation involves freeing and denaturing aggrecan inside the solution with guanidine hydrochloride. Guanidine hydrochloride is a chaotropic agent which reversibly denatures proteins and extracts them into a solution. The purpose of the guanidine is to keep aggrecan denatured in an extracted proteoglycan solution.

By using electrolysis, the ions then move from the solution and into the collagen matrix of the defective cartilage tissue. First, an electrical source, such as a battery, provides electricity 130. The solution containing ions and an area about the defective cartilage tissue are contacted with the electricity from the electrical source through various apparatus 140. Next, the electrical source is powered on whereby the ions move from the solution and into the defective cartilage tissue 150.

Figure 5:
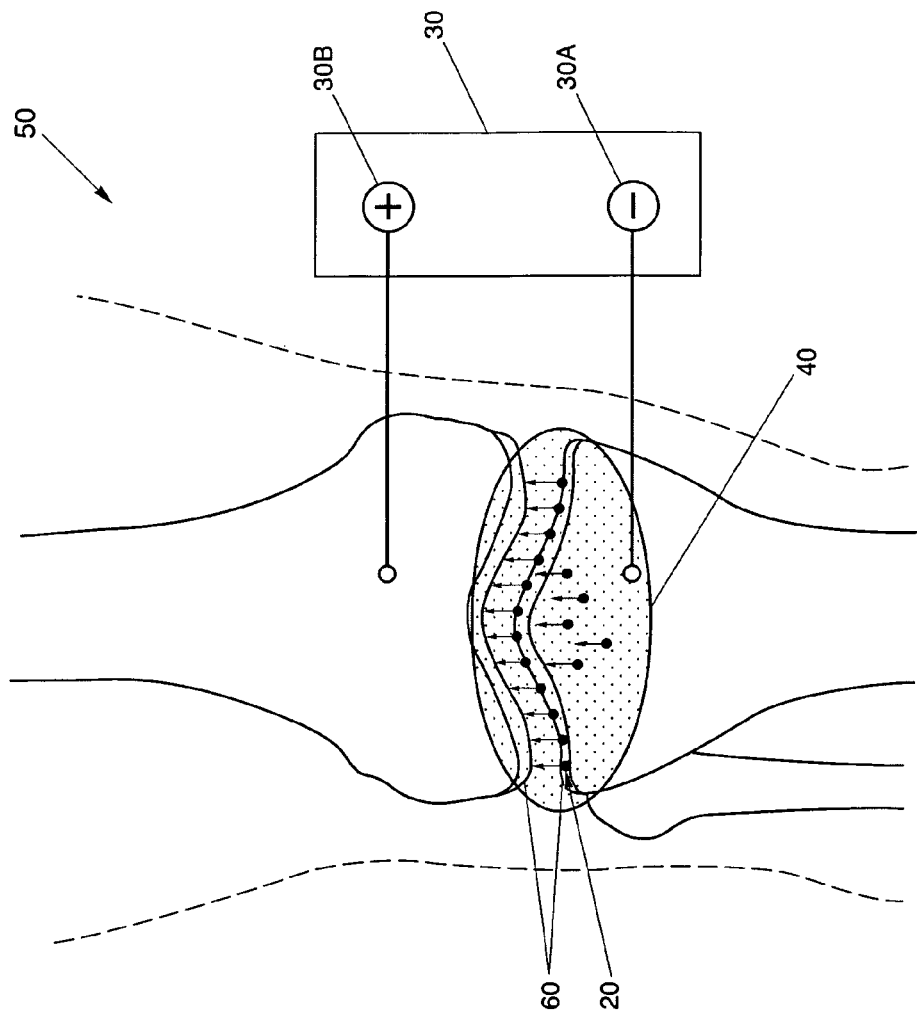
FIG. 5 is a partial cross-sectional view of a joint illustrating an example of method in FIG. 4.

Referring to FIG. 5, a partial cross-sectional view of a joint 50 having defective cartilage tissue 60 illustrates the method of FIG. 4. A solution 40 containing ions is provided and the ions 20 are negatively charged. An electrical source 30 is provided having a first end 30A, which is negative, and a second end 30B, which is positive. The first end 30A contacts the solution 40 containing the ions 20 and the second end 30B contacts the bone. When the electrical source 30 is powered on, the ions 20 move towards the second end 30B whereby the ions 20 then move from the solution 40 and into the defective cartilage tissue 150.

Figure 6:
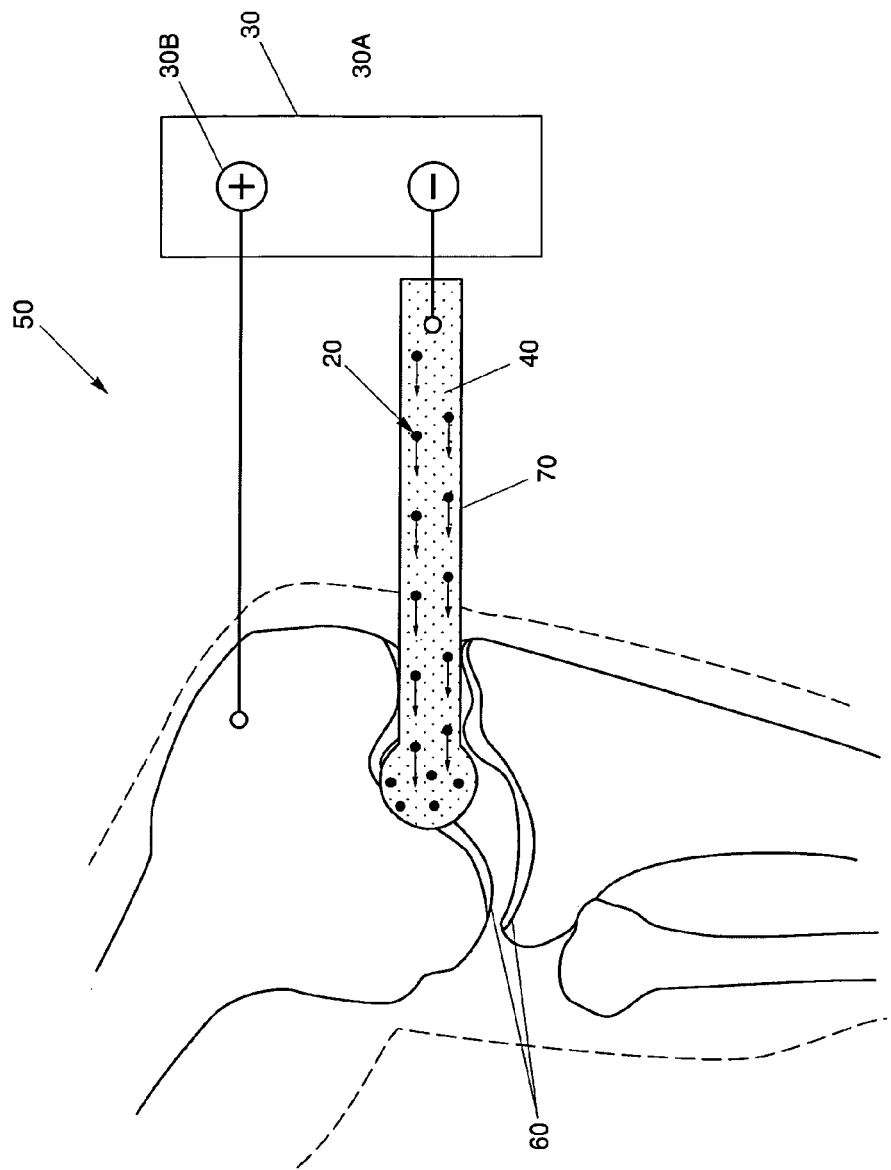
FIG. 6 is a partial cross-sectional view of a joint illustrating the use of an apparatus in performing the method of FIG. 4.
Figure 7:
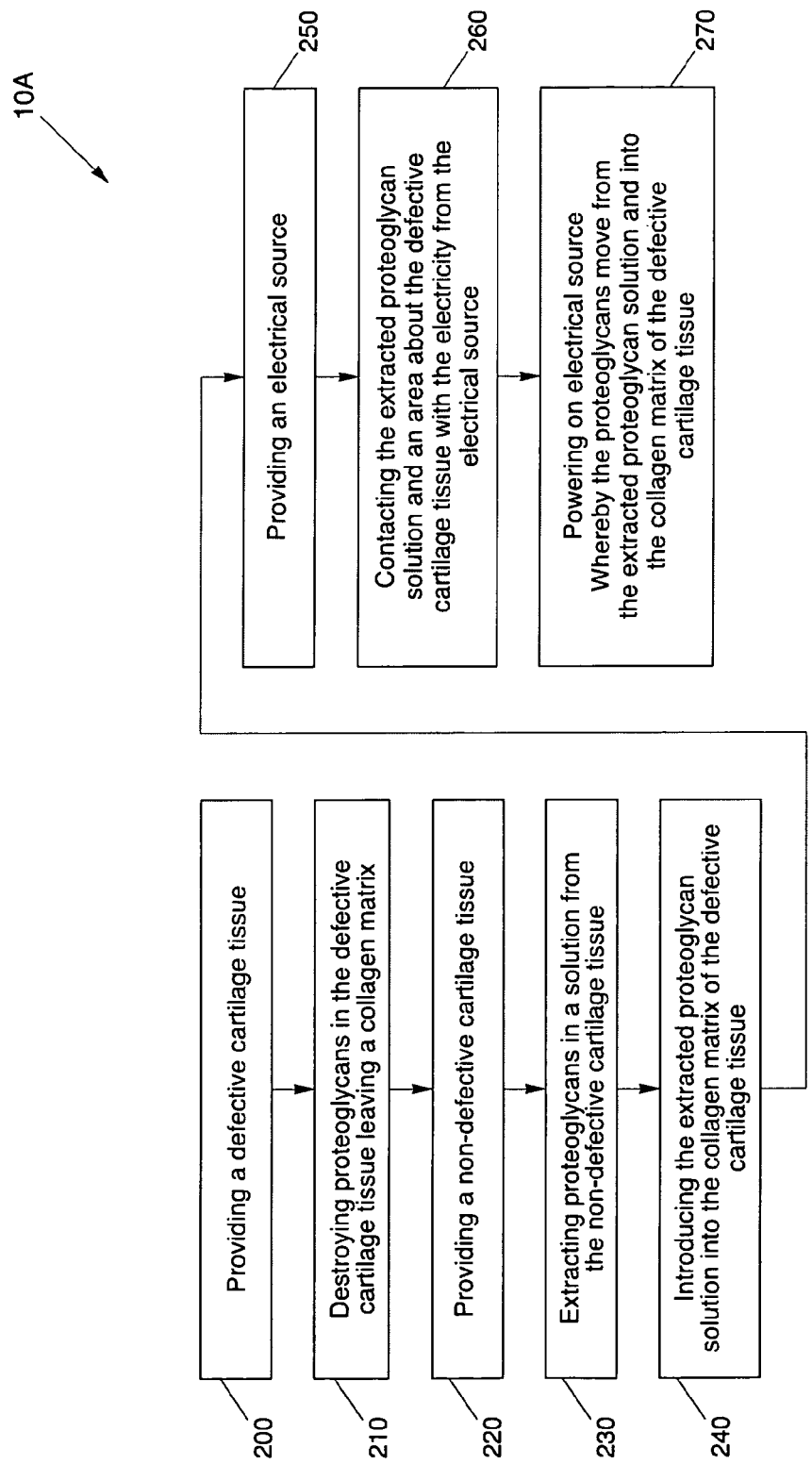
FIG. 7 is a block diagram of the method of treating cartilage defects using an extracted proteoglycan solution.

Referring to FIG. 6, in one embodiment of the present invention, the method for treating cartilage defects 10 is performed using an apparatus 70, such as a probe. Typically, the apparatus 70 would be used during arthroscopic surgery. In addition to the steps above, the apparatus 70 is filled with the solution 40 containing ions 20 for treating cartilage defects. In one embodiment, the ions 20 are negatively charged. It should be noted the ions 20 may be negatively or positively charged.

The first end 30A of the electrical source 30 is connected to the apparatus 70 filled with solution 40 containing ions 20. In one embodiment, the first end 30A of the electrical source 30 is negative. A second end 30B of the electrical source 30 contacts an area about the defective cartilage tissue 60, such as bone.

Next, the apparatus 70 contacts the defective cartilage tissue 60 and the electrical source 30 is powered on. When the electrical source 30 is powered on, the negatively charged ions 20 move out of the apparatus 70 towards the second end 30B, and into the collagen matrix of the defective cartilage tissue 60. It should be noted that the positions and usage of the first end 30A and second end 30B may vary depending on whether the ions 20 are either negatively or positively charged to move the ions 20 into the collagen matrix of the defective cartilage tissue 60.

The method for treating cartilage defects 10 may also be performed in a laboratory setting as outlined in the method 10A below. A defective cartilage tissue is provided having a collagen matrix and an absence of proteoglycans 200. First, proteoglycans in the defective cartilage tissue are destroyed leaving behind a collagen matrix 210. In one embodiment, the proteoglycans in the defective cartilage tissue are destroyed by trypsinization.

Next, a non-defective cartilage tissue is provided either natural, synthesized, or a product of tissue engineering 220. The proteoglycans are then extracted in a solution from the non-defective cartilage tissue using guanidinization 230. The extracted proteoglycan solution is then introduced into the collagen matrix of the defective cartilage tissue 240. It should be noted that the solution may be selected from a group consisting: proteoglycan solution, aggrecan isolation, chondrotin sulfate, glucosamine, or combinations thereof.

By using electrolysis, the proteoglycans then move from the proteoglycan solution and into the collagen matrix of the defective cartilage tissue. First, an electrical source, such as a battery, provides electricity 250. The extracted proteoglycan solution and an area about the defective cartilage tissue contacts the electricity from the electrical source 260. The electrical source is then powered on whereby the proteoglycans move from the extracted proteoglycan solution and into the collagen matrix of the defective cartilage tissue 270.

In one experiment, for example, trypsinization of 1 g of defective cartilage tissue is performed for twenty-four hours at 37 degrees Celsius. The trypsin destroys the proteoglycans but leaves the collagen matrix intact. The guanidinization of 1 g non-defective cartilage tissue is performed for 48 hours at pH 6.3. The guanidine hydrochloride releases the proteoglycans, containing aggrecans, into the solution in a denatured state. Next, the trypsinized defective cartilage tissue is introduced into the extracted proteoglycan solution. Using electricity, the proteoglycans of the extracted proteoglycan solution are moved into the trypsinized defective cartilage tissue.

In one embodiment, the defective cartilage tissue is dialyzed to remove the guanidine to allow aggrecan to reaggregate. Without being bound to any particular theory, it is believed that after the defective cartilage tissue is dialyzed, it will then remove the guanidine to allow the aggrecan to reaggregate. According to the prior art, the aggrecan stays in the collagen matrix by its shear size or by chemical interactions or chemical bonding which keep the aggrecans from leaving the collagen matrix.

Therefore, the present invention provides a method for treating cartilage defects. More specifically, the present invention relates to a method for treating cartilage defects by moving ions into the collagen matrix of the defective cartilage area using electricity. The method for treating cartilage defects maintains a balance between the three phases of cartilage. The method for treating cartilage defects has minimal adverse side effects. The method for treating cartilage defects provide a method which controls pain, improves joint function, maintains normal body weight, and achieves a healthy lifestyle. It is contemplated that this process may also be used for scaffolds and matrices.

It would be appreciated by those skilled in the art that various changes and modifications can be made to the illustrated embodiments without departing from the spirit of the present invention. All such modifications and changes are intended to be covered by the appended claims and the present invention.

What is claimed is:

1. A method for treating cartilage defects, comprising the steps of:
   providing a defective cartilage tissue which has a collagen matrix and an absence of proteoglycans;
   providing an solution containing charged ions for treating defective cartilage tissue, the solution containing charged ions is selected from a group consisting of: proteoglycan solution, aggrecan isolation, chondrotin sulfate, glucosamine or combinations thereof;
   injecting the solution containing the charged ions into the collagen matrix of the defective cartilage tissue;
   providing an electrical source generating electricity having a first end and a second end;
   contacting a first end of the electrical source to an area proximal to the defective cartilage tissue and bone area
   contacting a second end of the electrical source to the solution containing charged ions;
   providing electricity to the first end moving charged ions towards the first end and out of the solution containing ions;
   providing electricity to the second end moving charged ions towards the first end and into the defective cartilage tissue to replace the absent proteoglycans,
   whereby the charged ions move from the solution and back into the defective cartilage tissue to provide healthier cartilage tissue.

2. The method of claim 1, wherein the cartilage defect is selected from a group consisting of: osteoarthritis, rheumatoid arthritis, cartilage injury, and other cartilage defects.

3. The method of claim 1, wherein the proteoglycan solution is extracted from a non-defective cartilage tissue.

4. The method of claim 3, wherein the proteoglycans are extracted into a solution from the non-defective cartilage tissue by guanidinization.

5. The method of claim 3, wherein the non-defective cartilage tissue is natural cartilage.

6. The method of claim 3, wherein the non-defective cartilage tissue is synthesized.

7. The method of claim 4, further comprising:
   the defective cartilage tissue is dialyzed to remove the guanidine to allow aggrecan to reaggregate.

8. The method of claim 1, further comprising:
   providing an apparatus;
   filling the apparatus with the solution containing ions for treating cartilage defects;
   connecting a first end of the electrical source to the apparatus containing the solution containing ions;
   contacting defective cartilage tissue with the apparatus; and
   contacting a second end of the electrical source to an area about the defective cartilage tissue.

9. The method of claim 8, wherein the first end of the electrical source is anode.

10. The method of claim 8, wherein the second end of the electrical source is cathode.

11. The method of claim 8, wherein the ions are negatively charged ions.

12. The method of claim 1, wherein the solution containing ions is an exogeneous solution containing ions.

13. The method of claim 1, wherein the solution containing ions is from a source other than the defective cartilage tissue.

14. A method for treating cartilage defects using electrolysis, comprising the steps of:
    providing a defective cartilage tissue which has a collagen matrix and an absence of proteoglycans;
    extracting a proteoglycan solution from a non-defective cartilage tissue;
    injecting the extracted proteoglycan solution containing negatively charged ions into the collagen matrix of the defective cartilage tissue;
    providing an electrical source generating electricity having a first positive end and a second negative end;
    contacting a first positive end of the electrical source to an area proximal to the defective cartilage tissue and bone area
    contacting a second negative end of the electrical source to the extracted proteoglycan solution containing negatively charged ions, the second negative end and the first positive end located on opposing areas of the defective cartilage tissue;
    providing electricity to the first positive end attracting negatively charged ions towards the first positive end and out of the proteoglycan solution;
    providing electricity to the second negative end moving negatively charged ions away and towards the first positive end and into the defective cartilage tissue to replace the absent proteoglycans;
    whereby the negatively charged ions move from the proteoglycan solution and back into the defective cartilage tissue to provide healthier cartilage tissue.

15. The method of claim 14, wherein the proteoglycans are extracted into a solution from the non-defective cartilage tissue by guanidinization.

16. The method of claim 15, wherein the guanidinzation of the non-defective cartilage tissue is performed for 48 hours at a pH greater than 6.

17. The method of claim 14, wherein trypsinization of the defective cartilage tissue is performed to destroy the proteoglycans and leave the collage matrix intact.

18. The method of claim 17, wherein trypsinization is performed for twenty four hours at greater than 35 degrees Celsius.

19. The method of claim 14, wherein the defective cartilage tissue is dialyzed to remove the guanidine and to allow aggrecan to reaggregate.

* * * * *